United States Patent [19]

Hagihara et al.

[11] Patent Number: 5,008,012
[45] Date of Patent: Apr. 16, 1991

[54] COMPACT PLASMA SEPARATOR AND AN APPARATUS CONTAINING THE SAME

[75] Inventors: Takeaki Hagihara; Satoshi Aoki, both of Oita, Japan

[73] Assignee: Asahi Medical Co., Ltd., Tokyo, Japan

[21] Appl. No.: 357,167

[22] Filed: May 25, 1989

[51] Int. Cl.$^5$ ............................................. B01D 63/02
[52] U.S. Cl. ............................ 210/321.8; 210/321.89; 210/433.1; 604/6
[58] Field of Search ........... 210/321.79, 321.8, 321.88, 210/321.89, 433.1; 604/4, 5, 6

[56] References Cited

U.S. PATENT DOCUMENTS

| | | | |
|---|---|---|---|
| 4,381,775 | 5/1983 | Nose et al. | 210/805 |
| 4,401,567 | 8/1983 | Shindo et al. | 210/500.36 |
| 4,648,974 | 3/1987 | Rosskopf et al. | 210/651 |
| 4,668,399 | 5/1987 | Duggins | 210/651 |
| 4,696,748 | 9/1987 | Nitadori et al. | 210/321.89 |
| 4,729,829 | 3/1988 | Duggins | 210/651 |
| 4,869,822 | 9/1989 | Kamei et al. | 210/321.88 |

FOREIGN PATENT DOCUMENTS

| | | |
|---|---|---|
| 0050399 | 4/1982 | European Pat. Off. |
| 0114698 | 8/1984 | European Pat. Off. |
| 0120445 | 10/1984 | European Pat. Off. |
| 0112173 | 2/1986 | European Pat. Off. |

Primary Examiner—W. Gary Jones

[57] ABSTRACT

A compact plasma separator comprises a casing provided with a blood introduction opening, a blood withdrawal opening and at least one opening for plasma withdrawal. A bundle of porous hollow fibers is disposed in the casing and fluid-tightly connected at end portions thereof to the blood introduction opening and the blood withdrawal opening. The porous hollow fibers have an average effective length not greater than 200 mm and a membrane surface area not greater than 0.3 m$^2$, and the average effective length (L mm) satisfies the following relationship:

$$L/D^2 \text{ (mm}^{-1}) \geq 2000$$

in which D represents an average inner diameter of the porous hollow fibers. The compact plasma separator can easily be constructed into an apparatus which can be practically employed for separating plasma from whole blood. With this apparatus, plasma separation can be performed at a high plasma collection rate, without the danger of hemolysis at the time of plasma separating, without the danger of blood coagulation and without the danger of hollow clogging.

10 Claims, 3 Drawing Sheets

COMPACT PLASMA SEPARATOR AND AN APPARATUS CONTAINING THE SAME

BACKGROUND OF THE INVENTION

1. Field Of The Invention

The present invention relates to a compact plasma separator and an apparatus containing the same. More particularly, the present invention is concerned with a compact plasma separator comprising a casing provided with a blood introduction means, a blood withdrawal means and at least one opening for plasma withdrawal and a plurality of porous hollow fibers disposed in the casing, wherein the porous hollow fibers have an average effective length not greater than 200 mm and a membrane surface area not greater than 0.3 m$^2$, which average effective length is in a specific relationship with an average inner diameter of the porous hollow fibers The present invention is also concerned with an apparatus comprising the above-mentioned compact plasma separator having, connected thereto, a blood introducing passage means, a blood withdrawing passage means and a plasma withdrawing passage means.

By the use of the compact plasma separator and apparatus according to the present invention, effective, efficient separation of whole blood into plasma and blood corpuscles can be attained despite the small size of the plasma separator. A plasma collection rate, as defined later, of 60% or higher, is attained by the use of the compact plasma separator and apparatus according to the present invention.

2. Discussion of Related Art

In recent years, separation of blood by means of porous membranes is increasingly used in the field of medical treatment, in place of the conventional centrifugal separation method. Techniques for separating blood into various blood components according to a membrane separating method are especially used. Among such techniques, the technique using a plasma separator capable of separating blood into corpuscle components and plasma components is utilized for a variety of medical treatment purposes. An example of such medical treatment is found in plasma exchange therapy in which the plasma of a patient suffering from a disease caused by an abnormal plasma component is separated and discarded for replacement with fresh plasma from a healthy person. Another example of such medical treatment is found in plasma purification therapy in which the plasma is separated and purified and then returned to a patient. Further, examples of such medical treatment are found in plasma collection in which only the plasma is collected from a healthy person, and plasma separation from stored blood in which the stored blood is separated into blood corpuscle components and plasma components.

Various proposals have been made in the art for improving plasma collection rate in the separation of whole blood into plasma components and blood corpuscle components using porous membranes. For example, it was proposed to employ a porous membrane having a large surface area, e.g., a porous hollow fiber membrane having a surface area of at least 0.5 m$^2$. Further, a method in which a plasma collection rate is maximized by increasing the length of a plasma separator having hollow fibers disposed therein has been proposed. A method in which a blood recycle circuit containing a pump therein is provided in an extra-corporeal blood flow circuit comprising a plasma separator so that the blood is recycled through the plasma separator at an increased flow rate has also been proposed. Further, a method in which a porous membrane is rotated at a high speed so as to attain high shear rate has been proposed. However, these conventional methods have drawbacks because the amount of blood to be extracorporeally circulated is large, causing the burden upon the patients or volunteers to be high. Moreover, these conventional methods are disadvantageous because of a danger of hemolysis and because the handling of the apparatus is not easy.

Compact plasma separators are known in the art, which comprise a casing and porous hollow fiber membranes disposed therein. The membranes have a surface area of up to 0.3 m$^2$ and an average effective length of hollow fibers of up to 200 mm. However, performance for the known compact plasma separators has not been desirable. For example, Plasmapur (trade name of a plasma separator manufactured and sold by Organon Teknika N.V., the Netherlands) comprises a casing and, disposed therein, porous hollow fiber membranes of polypropylene having a membrane surface area of 0.07 m$^2$, an average effective length of hollow fibers of 150 mm and an average inner diameter of hollow fibers of 330 μm. The plasma collection rate defined later, as measured at a blood flow rate of 100 ml/min using an ACD-added bovine blood with a hematocrit value of 45%, is as low as 47.6%.

U.S. Pat. No. 4,668,399 (also U.S. Pat. No. 4,729,829 being a division of U.S. Pat. No. 4,668,399) discloses a compact plasma separator comprising porous hollow fibers, having a ratio (L/D) of effective length (L cm) to inner diameter (D cm) of not greater than 16,400 cm$^{-1}$ D, disposed within a casing having a blood inlet for conducting blood to the fibers, an outlet for conducting exit blood (plasma-depleted blood) from the fibers and a plasma outlet for conducting plasma out of the separator. In the plasma separator of this patent when used in the steady state flow mode, the blood flow rate is low so that the plasma separator exhibits poor plasma collection rate. Therefore, a recycle method and a pulsed flow method are also proposed in the U.S. patent for obtaining an increased yield of plasma, since in such methods, the blood flow rate can be increased. However, the recycle method and pulsed flow method described therein have drawbacks in that the apparatus is not simple, the operation is not easy, and the volume of the blood taken from a patient is inevitably large. Moreover, these methods have drawbacks because hemolysis is likely to occur in a pump for recycling which is employed in the methods, and because blood is likely to contact foreign materials due to the use of a pump for recycling, etc.

SUMMARY OF THE INVENTION

With a view toward developing a compact plasma separator which is free from the above-described drawbacks of the prior art, the present inventors have made extensive and intensive studies. As a result, it has unexpectedly been found that as illustrated in FIG. 3 (which will be explained later), a linear relationship exists between L/D$^2$ and the plasma collection rate of the plasma separator. In L/D$^2$, L represents the average effective length (mm) of hollow fibers disposed in a plasma separator and D represents the average inner diameter (mm) of the hollow fibers. That is, it has unexpectedly been found that as L/D$^2$ (mm$^{-1}$) is increased, the plasma collection rate linearly increases. In other words, it has unexpectedly been found that a compact plasma separator having a desirable plasma collection rate can be obtained by increasing the value of $L/D^2$. From a practical point of view, the value of $L/D^2$ may preferably be at least 2000 $mm^{-1}$. The present invention has been completed based on the above novel finding.

It is, therefore, an object of the present invention to provide a compact plasma separator by which plasma separation can be performed at a high plasma collection rate, without the danger of hemolysis at the time of plasma separating operation, and without the danger of blood coagulation and hollow clogging.

It is another object of the present invention to provide an apparatus containing a plasma separator of the above character.

The foregoing and other objects, features and advantages of the present invention will be apparent to those skilled in the art from the following detailed description and appended claims taken in connection with the accompanying drawings. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitative of the present invention, and wherein:

In FIGS. 1 through 4, like parts or portions are designated by like numerals.

DETAILED DESCRIPTION OF THE INVENTION

Figure 1:
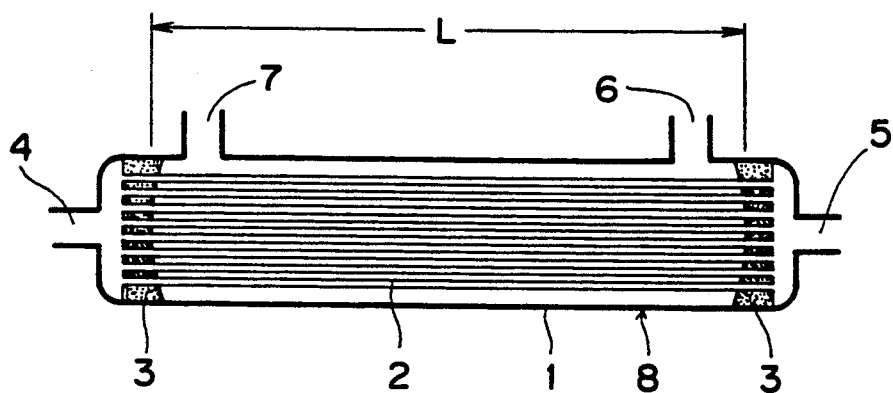
FIG. 1 is a diagrammatic cross-sectional view of one form of the compact plasma separator according to the present invention.

In the present invention, a compact plasma separator is provided with a casing having blood introduction means for introducing blood to the casing, blood withdrawal means for withdrawing blood from the casing and at least one opening for plasma withdrawal, and with a plurality of porous hollow fibers having substantially equal length. The fibers are arranged in a substantially parallel relationship and are bonded together at both end portions thereof to form a bundle. Each porous hollow fiber of the bundle has openings at both ends thereof. The bundle is disposed in the casing along the length of the casing, and both end portions of the hollow fibers of the bundle are fluid-tightly connected to the blood introduction means and the blood withdrawal means, respectively. The blood introduction means and the blood withdrawal means are thereby in communication through the bundle of hollow fibers. The porous hollow fibers have an average effective length (L mm) not greater than 200 mm and a membrane surface area (S m$^2$) not greater than 0.3 m$^2$. The average effective length (L mm) is defined as an average of the lengths of the porous hollow fibers minus the lengths of both end portions of the porous hollow fibers at which the fibers are bonded together and fluid-tightly connected to the blood introduction means and the blood withdrawal means, respectively.

The membrane surface area (S m$^2$) is defined by the formula:

$$S = n\pi DL \times 10^{-6}$$

wherein n is the number of porous hollow fibers, L is as defined above and D is an average inner diameter (mm) of the porous hollow fibers.

The average effective length (L mm) and the average inner diameter (D mm) satisfy the following relationship:

$$L/D^2 (mm^{-1}) \geq 2000.$$

As described above, in the present invention, it is essential that the average effective length (L mm) and the average inner diameter (D mm) of the porous hollow fibers satisfy the following relationship:

$$L/D^2 (mm^{-1}) \geq 2000.$$

With respect to this characteristic feature of the present invention, a further explanation will now be made.

The present inventors have prepared various porous hollow fibers having different inner diameters and disposed the prepared porous hollow fibers in various casings having different lengths to prepare various plasma separators. The porous hollow fibers disposed in each plasma separator have a membrane surface area not greater than 0.3 m$^2$ and an average effective length not greater than 200 mm, and the plasma separators have exhibited values of $L/D^2$ (wherein L represents an average effective length of the porous hollow fibers and D represents an average inner diameter of the porous hollow fibers) of from 1000 to 3500 $mm^{-1}$. Using each of the plasma separators, a plasma separation test has been performed, and then the plasma collection rate (hereinafter often abbreviated as "$R_{PC}$") of each of the plasma separators has been calculated by the following formula:

$$R_{PC} (\%) = \frac{F_P \times 100}{Q_B(1 - Ht \times 10^{-2})}$$

wherein $F_P$ represents the plasma filtration rate (ml/min) which is the amount of plasma filtered per minute by a plasma separator under a trans-membrane pressure of 50 mmHg, $Q_B$ represents the flow rate of introduced blood (ml/min), and Ht represents the hematocrit value (%) of blood.

Figure 3:
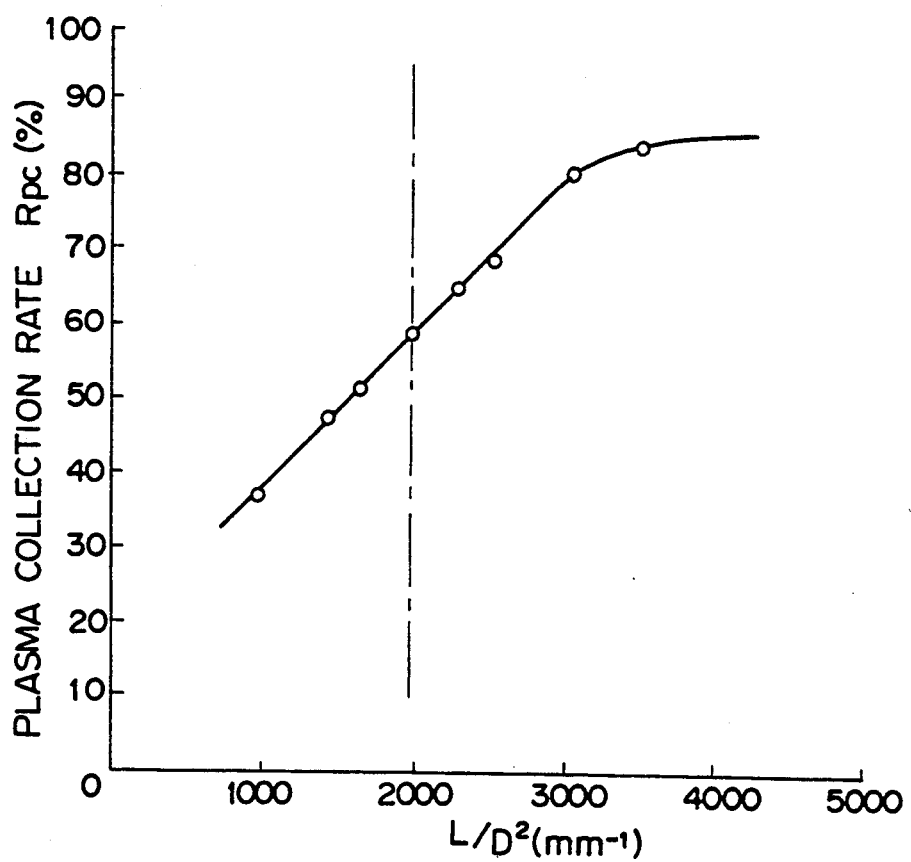
FIG. 3 is a graph showing the relationship between the value of $L/D^2$ as mentioned hereinbefore and the plasma collection rate of a plasma separator.

From the test results, it has unexpectedly been found that there is a linear relationship between $L/D^2$ ($mm^{-1}$) and the plasma collection rate ($R_{PC}$), as shown in FIG. 3. It has also been found that a plasma separator exhibiting a plasma collection rate as high as 60% or more can be obtained by the use of porous hollow fibers having an average effective length (L) and an average inner diameter (D) which satisfy the relationship $L/D^2 \geq 2000$ (mm$^{-1}$). As a result, the present inventors have found that by controlling the average effective length (L) and the average inner diameter (D) to satisfy the abovementioned relationship, it is possible to control the size of a plasma separator, and particularly, to minimize the size of a plasma separator which exhibits a plasma collection rate as high as 60% or more.

It is important that the plasma separator exhibits a plasma collection rate as high as 60% or more. This is understood from the following facts.

(1) There has been a strong demand in the art for a practical compact plasma separator (L: not greater than 200 mm, and membrane surface area: not greater than 0.3 m$^2$) having a plasma collection rate as high as 60% or more.

(2) In Gyomu Kijun (Business Standard) of the Japanese Red Cross Society, with respect to the apparatus for the separation of plasma from blood, there is a requirement that 90 ml of plasma should be separated from 230 ml of preserved blood (whole blood: 200 ml, preservative: 30 ml) and also a requirement for blood collection that the lower limit of Ht is about 40%. The plasma collection rate (RPC) necessary for obtaining 90 ml of plasma from 200 ml of whole blood having a Ht value of 40% can be calculated as follows.

$$R_{PC}(\%) = \frac{\text{volume of plasma obtained} \times 100}{\text{volume of whole blood} \times (1 - Ht \times 10^{-2}) + 30}$$

$$= \frac{90 \times 100}{200 \times (1 - 0.4) + 30}$$

$$= 60\%$$

(3) When a plasma separator is used for therapeutic purposes or separation of blood into plasma and blood cell components, it is preferred that plasma be collected in a short period of time in a large amount. Therefore, a high plasma collection rate, namely 60% or more, is preferred.

(4) In plasma separation using a centrifugal separator, the plasma collection rate is generally 60% or more. Accordingly, in view of the practical requirements, it is also critical for a compact plasma separator containing porous hollow fibers to exhibit a plasma collection rate of 60% or more.

The average effective length (L) is defined as an average of the lengths of the porous hollow fibers minus the lengths of both end portions of the porous hollow fibers at which the fibers are bonded together and fluid-tightly connected to the blood introduction means and the blood withdrawal means, respectively. Practically, a value of the average effective length is obtained by measuring the maximum effective length of porous hollow fibers (hereinafter referred to as "l max") and the minimum length of porous hollow fibers (hereinafter referred to as "l min"), adding l max and l min to obtain a sum thereof, and dividing the sum by 2 to obtain the average of l max and l min. This average is defined as the average effective length (L) in the present invention. The average inner diameter (D) is determined by averaging values of d's as defined below, using 30 porous hollow fibers. The "d" of each hollow fiber is determined by projecting an enlarged cross-section of the porous hollow fiber, for example, by means of a projector, measuring a major inner diameter of the projected porous hollow fiber and a minor inner diameter of the projected porous hollow fiber, calculating an actual major inner diameter of the porous hollow fiber (hereinafter referred to as "d max") and an actual minor inner diameter of the porous hollow fiber (hereinafter referred to as "d min"), adding d max and d min to obtain a sum thereof and dividing the sum by 2 to obtain the average of d max and d min, which is the abovementioned "d". The above measurement is conducted with respect to 30 porous hollow fibers which are arbitarily chosen. The 30 values of d's are averaged and the average value is defined as the average inner diameter (D) in the present invention. When the average effective length is 200 mm (which is the maximum of the average effective length range in the present invention), the maximum of the average inner diameter should be 0.316 mm for satisfying the relationship of $L/D^2(\text{mm}^{-1}) \geq 2000$. The size of a plasma separator can be decreased in length as well as in thickness as long as the relationship of $L/D^2(\text{mm}^{-1}) \geq 2000$ is satisfied.

As seen from FIG. 3, the plasma collection rate becomes nearly constant irrespective of the increase of the value of $L/D^2$ after the value of $L/D^2$ has reached a point of about 3000 mm$^{-1}$. However, the objective of the present invention is attained as long as the plasma collection rate is at least 60%.

Referring now to FIG. 1, a diagrammatic crosssectional view is shown of one form of the compact plasma separator of the present invention. The compact plasma separator comprises casing 1 provided with blood introduction means 4, blood withdrawal means 5 and opening 6 for plasma withdrawal. Additionally, the compact plasma separator may have opening 7 for monitoring pressure. The plasma separator contains a plurality of porous hollow fibers 2 substantially equal in length which are arranged substantially in parallel relationship and bonded together by means of adhesive 3 at both end portions thereof to form a bundle. The bonding of the end portions of the hollow fibers may alternatively be effected by fusion-bonding. Each porous hollow fiber 2 of the bundle has openings at both terminal ends thereof. The bundle is disposed in casing 1 along the length of the casing. Both end portions of hollow fibers 2 of the bundle are fluid-tightly connected by means of the adhesive to blood introduction means 4 and blood withdrawal means 5, respectively, thereby establishing communication between blood introduction means 4 and blood withdrawal means 5 through the bundle of hollow fibers 2.

The plasma separator of the present invention is used mainly for separating blood into a blood cell portion and a plasma portion. The practical utility of the separation of blood into a blood cell portion and a plasma portion includes, for example, therapeutic treatments, such as plasma exchange and purification of plasma; collection of plasma from healthy human beings; and separation of preserved blood. The plasma separator can also be used for separating body fluid into a liquid portion and a solid portion. For example, the plasma separator can be used as an ascites treating device for separating cancer cells from carcinomatous ascites. The compact plasma separator of the present invention can easily be constructed into an apparatus which can be practically employed for separating plasma from whole blood. Therefore, in another aspect of the present invention, a compact plasma separator apparatus is provided comprising:

(a) a compact plasma separator comprising:
  a casing provided with blood introduction means for introducing blood to the casing, blood withdrawal means for withdrawing blood from the casing and at least one opening for plasma withdrawal, and a plurality of porous hollow fibers substantially equal in length, said fibers being arranged in a substantially parallel relationship and being bonded together at both end portions thereof to form a bundle, each porous hollow fiber of the bundle having openings at both ends thereof, the bundle being disposed in the casing along the length of the casing, the both end portions of the hollow fibers of the bundle being fluid-tightly connected to the blood introduction means and the blood withdrawal means, respectively, the blood introduction means and the blood withdrawal means thereby being in communication through the bundle of hollow fibers, the porous hollow fibers having an average effective length (L mm) not greater than 200 mm and a membrane surface area (S m$^2$) not greater than 0.3 m$^2$, the average effective length (L mm) being defined as an average of the lengths of the porous hollow fibers minus the lengths of the both end portions of the porous hollow fibers at which the fibers are bonded together and fluid-tightly connected to the blood introduction means and the blood withdrawal means, respectively, the membrane surface area (S m$^2$) being defined by the formula:

$$S = n\pi DL \times 10^{-6}$$

wherein n is the number of porous hollow fibers, L is as defined above and D is an average inner diameter (mm) of the porous hollow fibers, the average effective length (L mm) and the average inner diameter (D mm) satisfying the following relationship:

$$L/D^2 (mm^{-1}) \geq 2000;$$

(b) blood introducing passage means for introducing blood to the blood introduction means, the blood introducing passage means comprising a first conduit having one end fluid-tightly connected to the blood introduction means of the plasma separator, a second conduit having a blood inlet at one end thereof, and means for transporting blood, the means for transporting blood being disposed between and fluid-tightly connected to the other ends of the first and second conduits;

(c) blood withdrawing passage means for withdrawing blood from the blood withdrawal means, the blood withdrawing passage means comprising a third conduit having one end fluid-tightly connected to the blood withdrawal means of the plasma separator and having a blood outlet at the other end thereof; and (d) plasma withdrawing passage means for withdrawing plasma from the opening for plasma withdrawal, the plasma withdrawing passage means comprising a fourth conduit having one end fluid-tightly connected to the opening for plasma withdrawal of the plasma separator and having a plasma outlet at the other end thereof.

Figure 2:
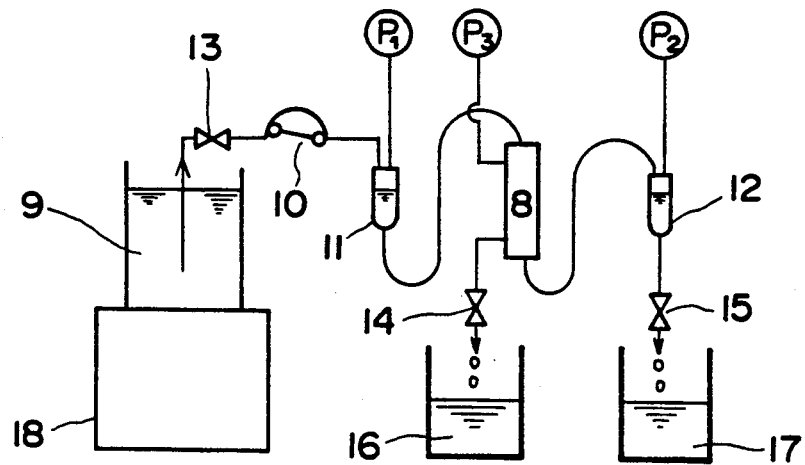
FIG. 2 is a diagrammatic view of one form of the compact plasma separator apparatus according to the present invention.

Referring to FIG. 2, one form of the compact plasma separator apparatus of the present invention is shown. The apparatus comprises (a) plasma separator 8 and (b) a blood introducing passage means with a first conduit having one end fluidtightly connected to the blood introduction means 4 (not shown) of plasma separator 8, a second conduit having a blood inlet 13 at one end thereof, and blood transport means 10 (e.g., pump) disposed between and fluid-tightly connected to the other ends of the first and second conduits through drip chamber 11. The apparatus also comprises (c) a blood withdrawal passage means with a third conduit having one end fluid-tightly connected to the blood withdrawal means 5 (not shown) of plasma separator 8 through drip chamber 12 and having blood outlet 15 at the other end thereof and (d) a plasma withdrawn passage means with a fourth conduit having one end fluid-tightly connected to the opening for plasma withdrawal 6 (not shown) of plasma separator 8 and having a plasma outlet 14 at the other end thereof.

In the present invention, it is preferred that the porous hollow fibers be composed of a membranous porous resin matrix having pores therewithin and openings on both surfaces thereof, the pores cooperating with the openings to form throughpaths running between both the surfaces of the resin matrix. The membranous porous resin matrix may be prepared from a hydrophilic material, such as cellulose, a cellulose derivative, a water-insoluble polyvinyl alcohol and a copolymer of ethylene and vinyl alcohol or a hydrophobic material, such as a polyolefin (e.g., polyethylene or polypropylene), a polysulfone and a polytetrafluoroethylene.

There is no particular limitation with respect to the porosity of the porous hollow fiber membrane to be used in the present invention. However, the porosity of the membrane is preferably in the range from 65% to 80%, and more preferably from 70% to 80%. This preferred range of porosity is high as compared to the ranges for porosities of the coventional membranes for plasma separation. The porosity is calculated using the pore volume of the membrane measured by means of a mercury porosimeter. When the porosity is less than 65%, the passage rate of plasma through pores of the membrane is likely to be the rate-determining step for the plasma collection rate. Therefore, for obtaining high plasma collection rate, application of a high trans-membrane pressure is required, which is practically disadvantageous. On the other hand, when the porosity exceeds 80%, the mechanical strength of the membrane becomes low, resulting in a danger of membrane breakage during plasma separation. Further, since the stiffness of the membrane becomes low, it is practically difficult for a porous hollow fiber made of the membrane disposed in a casing to maintain its hollow structure having a circular cross-section.

When the porosity is in the range from 70% to 80%, the plasma filtration rate $F_P$ increases as the trans-membrane pressure increases, but the plasma filtration rate $F_P$ reaches a plateau region at a point where the trans-membrane pressure becomes 50 mmHg. That is, $F_P$ does not depend on the transmembrane pressure but depends on factors other than the trans-membrane pressure.

Therefore taking into consideration the hereinbefore mentioned relationship $$R_{PC} (\%) = \frac{F_P \times 100}{Q_B (1 - Ht \times 10^{-2})},$$

the proportional relationship between $L/D^2$ and $R_{PC}$, when the porosity is in the range from 70% to 80%, $F_P$ under a trans-membrane pressure of 50 mmHg or more is almost in direct proportion to $Q_B(1-Ht\times 10^{-2})L/D^2$ irrespective of the trans-membrane pressure.

The average pore diameter of the porous hollow fibers to be used in the present invention is preferably in the range from 0.1 μm to 0.5 μm, and more preferably in the range from 0.1 μm to 0.45 μm. The plasma separator is required to be capable of separating the plasma component from the blood cell component. That is, the plasma separator is required to be capable of separating the constituent of the plasma component from the constituent of the blood cell component, both having sizes which are closest to each other, i.e., separating the largestsized constituent of the plasma component, i.e., high molecular weight protein substances having a size of several hundreds Å (e.g., 0.03 μm) from the smallest-sized constituent of the blood cell component, i.e., platelets having a size of 1 to 2 μm. For attaining such separation, the average pore diameter is preferably in the above-mentioned range of 0.1 μm to 0.5 μm.

The average pore diameter is determined as follows. The pore diameter and pore volume of the membrane are measured by means of a mercury porosimeter. The logarithm of the diameter is plotted as the abscissa and the pore volume is plotted as the ordinate to give a pore diameter distribution curve. Thus, the total pore volume is defined as an area defined by the abscissa and the pore diameter distribution curve. A vertical line is drawn parallel to the ordinate so that the total pore volume is halved. The value of the pore diameter on the abscissa at its point crossed by the abovementioned vertical line is referred to as the "average pore diameter". When the average pore diameter is 0.1 μm or more, the passage ratio of LDL (low-density lipoprotein, the estimated molecular size of which is 0.03 μm) which are the maximumsized constituent of the plasma component, is approximately 100%. When the average pore diameter is 0.5 μm or less, the passage ratio of platelets having a size of 1 μm or more is 0% in the case of a plasma separation membrane having a normal pore diameter distribution. Further, when plasma separation is performed by means of porous hollow fiber membranes having a maximum pore diameter of more than 0.5 μm at a TMP (trans-membrane pressure) of 75 mmHg, hemolysis is likely to be observed with respect to blood cells flowing through the hollow fiber membranes, while when plasma separation is performed by means of porous hollow fiber membranes having a maximum pore diameter of 0.5 μm or less, no hemolysis is observed. With a maximum pore diameter of 0.5 μm or less and an average pore diameter of 0.1 μm to 0.45 μm, a no-hemolysis pressure drop of 150 mmHg or more (a TMP of 75 mmHg or more) is attained, thereby making it possible to produce a compact plasma separator free from the danger of causing hemolysis.

The terminology "maximum pore diameter" used herein means a maximum pore diameter that is determined by a method described below, according to the principle of ASTM-F316-70. That is, air pressure is applied to the inside of a porous hollow fiber immersed in ethanol while increasing the air pressure, and the pressure at which air bubbles occur on the outer wall surface of the hollow fiber is taken as the bubble point pressure. The bubble point pressure is converted using a formula given in ASTM-F316-70 to a pore diameter, which is referred to as the "maximum pore diameter".

In general, when blood flows into porous hollow fibers, the hematocrit value of the blood is increased as the plasma component passes through the fiber membrane wall, and thus the resistance to the passage of the blood is increased. This increased resistance, in turn, increases the filtration pressure. Thus, not only is the danger of hemolysis increased but hollow clogging is also likely to occur, thereby causing a decrease with time in the plasma flux to occur. However, the decrease with time in the plasma flux can almost be completely prevented by using the compact plasma separator of the present invention in which porous hollow fibers having an average pore diameter in the range of from 0.1 to 0.45 μm are employed.

The average inner diameter of the porous hollow fibers to be used in the present invention is preferably in the range from 100 μm to 316 μm. As shown in FIG. 3, there exists a linear relationship between $L/D^2$ (mm$^{-1}$) and plasma collection rate, and in producing a compact plasma separator (L=200 mm or less, S=0.3 m² or less) having a high plasma collection rate, the smaller the inner diameter of the hollow fiber, the better the results which are obtained. When a plasma collection rate as high as 60% or more is to be attained, the inner diameter of the hollow fiber is required to be 316 μm or less, as apparent from the relationship of $L/D^2 \geq 2000$. On the other hand, if the inner diameter is less than 100 μm, the pressure loss of the blood along the fiber length is likely to be disadvantageously high.

Using the compact plasma separator apparatus as shown in FIG. 2, a plasma collection rate is measured as follows. That is, while stirring with a magnetic stirrer 18, ACD-added fresh bovine blood 9 ($Ht=35\pm2\%$) is caused to flow at a flow rate ($Q_B$) of $50\pm5$ ml/min into plasma separator 8, through pressure gauge $P_1$. The pressure gauge $P_1$ measures blood pressure of the blood introduced into the plasma separator by means of blood transport means 10, for example, a pump. The blood pressure of the blood withdrawn from the plasma separator, which blood pressure is measured by pressure gauge $P_2$ connected to drip chamber 12, is adjusted to 0 mmHg by means of blood outlet 15, for example, by a screw cock connected to the blood withdrawal means of the plasma separator. Thus, the blood is separated into plasma and blood cell-enriched blood by plasma separator 8. Plasma 16 and blood cell-enriched blood 17 are collected separately. The plasma filtration rate ($F_P$)(ml/min) is measured, and the plasma collection rate ($R_{PC}$) is determined according to the formula mentioned before. The results are shown in Table 3.

The transmembrane pressure (TMP) mentioned hereinbefore is determined as follows. The blood pressure on the blood introduction side of the plasma separator [hereinafter referred to as "pressure (A)"], the blood pressure on the blood withdrawal side of the plasma separator [hereinafter referred to as "pressure (B)"] and the plasma pressure [hereinafter referred to as "pressure (C)"] are measured by means of pressure gauges $P_1$ connected to drip chamber 11, $P_2$ connected to drip chamber 12 and $P_3$ connected to opening 7 (FIG. 1) for monitoring plasma pressure. From these blood pressures (A), (B) and (C), the TMP is calculated by the formula $(A-B)/2-C$.

The "membrane surface area (S)" mentioned herein is defined by the formula:

$$S = n\pi DL$$

wherein L is the average effective length of hollow fibers, D is the average inner diameter of hollow fibers and n is the number of hollow fibers.

From the viewpoint of releaving the burden on the patient, the amount of the blood to be drawn out of the body of the patient at one time is preferably minimized and, therefore, it is preferred that the surface area of the membrane is small. Moreover, blood taken from a living body exhibits various unfavorable vital reactions when it contacts foreign substances. By minimizing the membrane surface area, the danger of such unfavorable reactions can also be minimized. The membrane surface area is not greater than 0.3 m$^2$ in the present invention.

There is no particular limitation with respect to the method for forming a porous hollow fiber. A porous hollow fiber can be formed by a conventional method, such as wet spinning, dry spinning, melt spinning or the like. With respect to a porous hollow fiber obtained by wet spinning, although it is conventionally employed for a plasma separator, it has the danger of elusion of additives or an organic solvent, and is poor in tensile properties. Further, when wet spinning is employed for producing a hollow fiber having an inner diameter as small as 100 μm to 316 μm as in the present invention, controlling of the pore diameter of hollow fiber is not easy since the coagulation control for the inner wall of the hollow fiber is inherently difficult in wet spinning. A preferred method for producing a hollow fiber to be used in the present invention is a thermoforming process (see, U.S. Pat. No. 4,401,567). A stretching perforation method is particularly preferred in which a crystalline polymer is spun, e.g., by melt spinning, and subjected to cold stretching to cause cleavage among crystalline lamellae of the polymer and then subjected to hot stretching to attain an expansion of the cleavage. In this method, a perforated structure is produced by application of a physical process of stretching, without addition of any additives or a solvent, to the polymer material. This method is preferred because controlling of the pore diameter of a hollow fiber is easy, because there is no problem of a remaining solvent, and because the mechanical strength of the obtained hollow fiber is high due to the orientation of the molecules irrespective of the presence of a large number of pores.

As described above, the compact plasma separator of the present invention can easily be constructed into an apparatus which can be practically employed for separating plasma from whole blood. With this apparatus, plasma separation can be performed at a high plasma collection rate, without the danger of hemolysis at the time of plasma separating operation as well as the danger of blood coagulation and hollow clogging.

DETAILED DESCRIPTION OF THE PREFERRED EMBODIMENTS

The present invention will now be described in more detail with reference to Examples and Comparative Examples, which should not be construed to be limiting of the scope of the present invention. Examples 1 to 5 and Comparative Examples 1 to 3

A high-density polyethylene (HI-ZEX 2208J, a product of Mitsui Petrochemical Co., Japan) having a density of 0.968 g/cm$^3$ and a melt index, as measured in accordance with ASTM D1238, of 5.5 is extruded from an annular hollow fiber spinning nozzle having an annular orifice outside diameter of 34 mm and an annular orifice inside diameter of 26 mm (slit width: 4 mm) at an extruding temperature of 150° C. and at a polymer extrusion rate of 16 g/min and a winding rate of 230 m/min. The thus obtained hollow fiber is subjected to annealing at 115° C. for 2 hours. The annealed hollow fiber is then cold-stretched at room temperature at a stretching ratio (the ratio of the length of the stretched hollow fiber to the length of the hollow fiber before stretching, expressed by times) of 1.33 times by passing the annealed hollow fiber through stretching rolls arranged to provide a stretching path of 200 mm. Then, the cold-stretched hollow fiber is hot-stretched successively at 78° C., 95° C. and 98° C. at stretching ratios at 78° C., 95° C. and 98° C. of 3 times, 1.28 times and 1.14 times, respectively. The ratio (%) of the length of the stretched hollow fiber to the original length of the hollow fiber before cold-stretching and hot-stretching is 480%. The thus stretched hollow fiber is heat set at 115° C. for 2 min, to thereby obtain a porous polyethylene hollow fiber.

The polyethylene hollow fiber is immersed in a solution of a polyethylene vinyl alcohol (Soanol Z, manufactured and sold by The Nippon Synthetic Chemicals Industry Co., Ltd., Japan) having an ethylene content of 29% by mole, in 60% (v/v) aqueous ethanol solution, having a polyethylene vinyl alcohol concentration of 1.0% by weight, and kept at 55° C. for 1 min in the solution. Then, the hollow fiber is taken out of the solution and air-dried at 60° C. for 1.5 hours. The resultant hollow fiber has an average inner diameter (D) of 0.310 mm and a porosity of 73%. The hollow fiber is cut to an appropriate length for attaining an average effective length of hollow fibers of 190 mm when the hollow fibers are bonded to form a bundle as will be described below, to thereby obtain 1000 cut hollow fibers. A bundle of 1000 cut hollow fibers is inserted in a polycarbonate-made cylindrical casing having an opening for plasma withdrawal and an opening to be connected to a plasma pressure gauge on its side wall, so that the fibers are arranged in a substantially parallel relationship and disposed in the casing along the length thereof. Then, both end portions of the hollow fibers of the bundle and both end portions of the inner side wall of the polycarbonate-made cylindrical casing are bonded by a centrifugal molding method using an epoxy resin adhesive to obtain an assembly. Both end portions of the resultant assembly are cut off to open the ends of the hollow fibers, and an opening-having end cap is then attached to each of the end portions of the assembly as shown in FIG. 1 to provide a blood introduction means and a blood withdrawal means so that both end portions of the hollow fibers are fluid-tightly connected to the blood introduction means and the blood withdrawal means, respectively. As a result, the blood introduction means and the blood withdrawal means are in communication through the bundle of the hollow fibers. Thus, there is obtained a plasma separator as shown in FIG. 1. The average effective length (L) of the hollow fibers of the plasma separator is 190 mm, and the ratio of the average effective length of the hollow fibers to the square of the average inner diameter of the hollow fiber (L/D$^2$)=2000 mm$^{-1}$.

Using the thus obtained plasma separator, a plasma separation apparatus as shown in FIG. 2 is constructed, and the plasma collection rate is measured as follows. That is, an ACD-added fresh bovine blood 9 (Ht=35±2%) is caused to flow into the plasma separator 8, through pressure gauge P$_1$ for measuring blood pressure of the blood which is introduced into the plasma separator, by means of pump 10, at a flow rate ($Q_B$) of 50 ml/min. The blood pressure of the blood withdrawn from the plasma separator, which blood pressure is measured by pressure gauge $P_2$, is adjusted to 0 mmHg by means of screw cock 15 connected to the blood withdrawal means of the plasma separator. Thus, the blood is separated into plasma and blood cell-enriched blood by plasma separator 8, and the plasma 16 and the blood cell-enriched blood 17 are collected separately. The plasma filtration rate ($F_P$)(ml/min) is measured, and the plasma collection rate ($R_{PC}$) is determined according to the formula mentioned hereinbefore. Further, the Ht value of the blood cell-enriched blood is determined in the same manner as mentioned hereinbefore. The results are shown in Table 1.

Substantially the same procedure as mentioned above is repeated except that the annular orifice outside diameter, the annular orifice inside diameter and a winding rate are changed to those shown in Table 1, to thereby obtain various hollow fibers having different inner diameters as shown in Table 1. Using the hollow fibers, plasma separators having different average effective lengths of hollow fibers as shown in Table 1 are individually prepared. Then, using each of the plasma separators, the plasma separation apparatus as shown in FIG. 2 are individually constructed, and bovine blood is separated into plasma and blood cell-enriched blood by means of the apparatus in the same manner as mentioned above. Further, the plasma collection rate ($R_{PC}$) of the blood cell-enriched blood is determined in the same manner as mentioned above.

Based on the data shown in Table 1, the relationship between the plasma collection rate ($R_{PC}$) and the $L/D^2$ value is represented by the graph shown in FIG. 3. As apparent from FIG. 3, when the $L/D^2$ value is 1000 to 3000 mm$^{-1}$, there is a linear relationship. Further, it is apparent from FIG. 3 that for attaining a plasma collection rate of at least 60%, it is necessary to use a hollow fiber having an $L/D^2$ value of 2000 mm$^{-1}$ or more.

Moreover, it is also apparent that although the average effective length of hollow fibers of the plasma separator of the present invention is small, a high plasma collection rate is attained. Particularly, the plasma separator of Example 5 is extremely compact, that is, the average effective length of hollow fibers is 90 mm and the diameter of the plasma separator is 7.5 mm. Even by the use of this plasma separator, an extremely high plasma collection rate, that is, a plasma collection rate as high as 86%, is attained.

On the other hand, the plasma separator of Comparative Example 1 having an $L/D^2$ value of 1700 mm$^{-1}$ has a large size, that is, the average effective length of hollow fibers is 230 mm and the diameter of the plasma separator is 18 mm. Nevertheless, the plasma collection rate is not high, namely, only 53%.

TABLE 1

| | Outside diameter of spinning nozzle (mm) | Inside diameter of spinning nozzle (mm) | Winding rate (m/min) | Average inner diameter of hollow fiber (D, mm) | Average effective length of hollow fiber (L, mm) | Surface area of hollow fibers (m$^2$) | Porosity of hollow fiber (%) | $L/D^2$ (mm$^{-1}$) | $R_{PC}$ (%) | Ht value of blood cell-enriched blood (%) |
|---|---|---|---|---|---|---|---|---|---|---|
| Example 1 | 34 | 26 | 230 | 0.310 | 190 | 0.19 | 73 | 2000 | 60 | 57 |
| Example 2 | 34 | 26 | 280 | 0.280 | 180 | 0.16 | 75 | 2300 | 66 | 61 |
| Example 3 | 35 | 25 | 400 | 0.240 | 150 | 0.12 | 72 | 2600 | 68 | 62 |
| Example 4 | 35 | 25 | 500 | 0.200 | 125 | 0.08 | 73 | 3100 | 80 | 73 |
| Example 5 | 35 | 25 | 600 | 0.160 | 90 | 0.05 | 72 | 3500 | 86 | 80 |
| Comparative Example 1 | 34 | 26 | 200 | 0.370 | 230 | 0.26 | 74 | 1700 | 53 | 53 |
| Comparative Example 2 | 34 | 26 | 215 | 0.340 | 160 | 0.17 | 74 | 1400 | 48 | 51 |
| Comparative Example 3 | 34 | 26 | 220 | 0.330 | 110 | 0.11 | 73 | 1000 | 38 | 47 |

EXAMPLES 6 TO 10 AND COMPARATIVE EXAMPLES 4 TO 6

Substantially the same procedure as in Example 1 is repeated except that the hot-stretching temperatures are changed as shown in Table 2 to obtain various plasma separators having different average pore diameters and different maximum pore diameters as shown in Table 2 and each having an average effective hollow fiber length of 200 mm and an average hollow fiber inner diameter of 290±10 μm. Using each of the plasma separators, blood is separated into plasma and blood cell-enriched blood in substantially the same manner as in Example 1, except that the trans-membrane pressure (TMP) is stepwise increased from 25 to 50, 75, 100, 150, 200, 250 and finally 300 mmHg and the hemoglobin (Hb) concentration of the collected plasma is determined under the respective TMP using a customary hemoglobinometer. Incidentally, the TMP is determined as follows. The blood pressure (A) on the blood introduction side of the plasma separator, the blood pressure (B) on the blood withdrawal side of the plasma separator and the plasma pressure (C) are measured by means of pressure gauges $P_1$, $P_2$ and $P_3$. From these blood pressures (A), (B) and (C), the TMP is calculated by the formula: (A−B)/2−C. The Hb concentrations of the plasma are compared with the free Hb concentration of the original fresh bovine blood. If no significant difference is observed between the Hb concentration of the collected plasma and the free Hb concentration of the original fresh bovine blood, this means that the hemolysis of the blood is not caused during the plasma separation. However, if there is a significant difference, this means that the hemolysis is caused. By the comparison of the Hb concentrations of the plasma obtained under various TMP's with the free Hb concentration of the original fresh bovine blood, the maximum TMP under which no hemolysis is caused is determined (hereinafter referred to as "hemolytic pressure"). The results are shown in Table 2. Based on the results shown in Table 2, the relationship between the maximum pore diameter of the hollow fiber and the hemolytic pressure is indicated on the graph shown in FIG. 4.

Further, the permeability of low-density lipoprotein (LDL) is determined under the above-mentioned hemolytic pressure. The LDL is a representative example of high molecular weight proteins present in a plasma.

Therefore, the LDL permeability is useful as a criterion for evaluating whether or not substantially all of the components of plasma are passed through the membrane. The determination of the LDL permeability is conducted as follows The LDL concentration (E) of the original fresh bovine blood and the LDL concentration (F) of the collected plasma are determined by nephelometry (Scholnick H. R., Burstein, M. & Eder, H. A. : A simple method for the detection and identification of various types of hyperliporoteinemia, Protides Biol. Fluids, 19 : 289, 1972). The LDL permeability (%) is calculated by the formula: $F/E \times 100$. The results are shown in Table 2.

TABLE 2

|  | Hot-stretching temperature (°C.) 1st/2nd/3rd | Average pore diameter of hollow fiber membrane ($\mu$m) | Maximum pore diameter of hollow fiber membrane ($\mu$m) | Hemolytic pressure (mmHg) | LDL permeability (%) |
| --- | --- | --- | --- | --- | --- |
| Example 6 | 90/107/110 | 0.44 | 0.50 | 75 | 99 |
| Example 7 | 84/101/104 | 0.38 | 0.43 | 150 | 100 |
| Example 8 | 78/95/98 | 0.31 | 0.36 | 250 | 98 |
| Example 9 | 78/92/95 | 0.23 | 0.30 | >300 | 100 |
| Example 10 | 75/92/95 | 0.14 | 0.21 | >300 | 96 |
| Comparative Example 4 | 96/113/116 | 0.52 | 0.83 | 25 | 99 |
| Comparative Example 5 | 96/110/116 | 0.51 | 0.58 | 50 | 98 |
| Comparative Example 6 | 70/87/90 | 0.08 | 0.14 | >300 | 64 |

Figure 4:
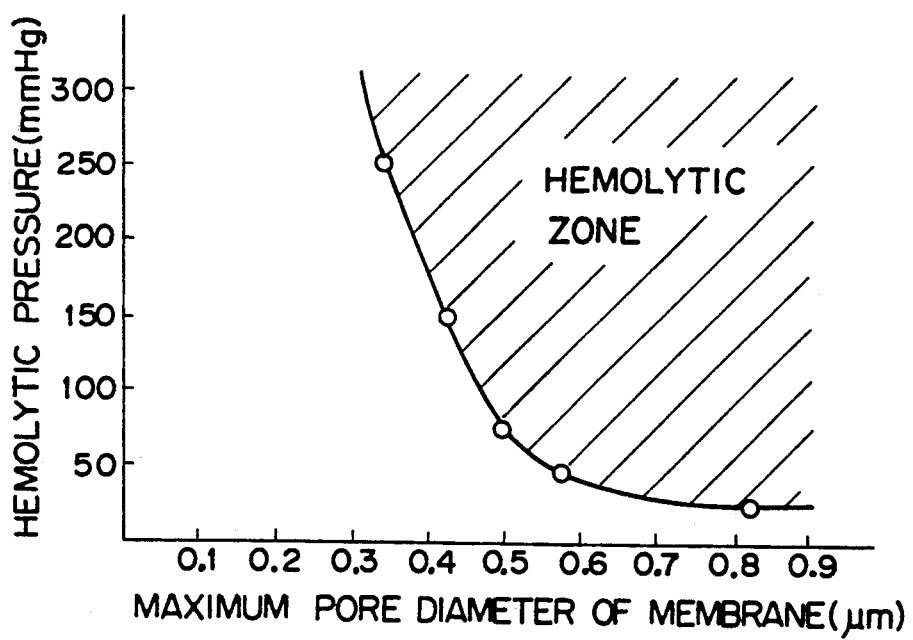
FIG. 4 is a graph showing the relationship between the maximum pore diameter of porous hollow fibers and the hemolytic pressure as defined later.

As apparent from Table 2 and FIG. 4, when the maximum pore diameter of the hollow fiber membrane is not greater than 0.5 $\mu$m, the hemolytic pressure is 50 mmHg or higher. That is, a relatively high blood pressure can be exerted to conduct plasma separation and, therefore, the plasma separation can be conducted with high efficiency. This means that when the maximum pore diameter of the hollow fibers is not greater than 0.5 $\mu$m, even if the average effective length of hollow fibers is short, a satisfactory plasma collection rate can be obtained without causing the hemolysis to occur. Therefore, a compact plasma separator can be obtained.

Further, as apparent from Table 2, when the average pore diameter of the hollow fiber is 0.1 $\mu$m or larger, a substantially whole amount (96 to 100%) of the LDL is passed through the hollow fiber membranes. This means that all the components of plasma are passed through the hollow fiber membranes.

EXAMPLE 11

A high-density polyethylene (HI-ZEX 2208J, a product of Mitsui Petrochemical Co., Japan) having a density of 0.968 g/cm$^3$ and a melt index, as measured in accordance with ASTM D1238, of 5.5 is extruded from an annular hollow fiber spinning nozzle having an annular orifice outside diameter of 35 mm and an annular orifice inner diameter of 25 mm (slit width: 5 mm) at an extruding temperature of 150° C. and at a polymer extrusion rate of 15 g/min and a winding rate of 500 m/min. The thus obtained hollow fiber is subjected to annealing at 115° C. for 2 hours. The annealed hollow fiber is then cold-stretched at room temperature at a stretching ratio (the ratio of the length of the stretched hollow fiber to the length of the hollow fiber before stretching, expressed by times) of 1.33 times by passing the annealed hollow fiber through stretching rolls arranged to provide a stretching path of 200 mm. Then, the cold-stretched hollow fiber is hot-stretched successively at 78° C., 95° C. and 98° C. at stretching ratios at 78° C., 95° C. and 98° C. of 3 times, 1.28 times and 1.14 times, respectively. The ratio (%) of the length of the stretched hollow fiber to the original length of the hollow fiber before cold-stretching and hot-stretching is 480%. The thus stretched porous hollow fiber is immersed in a polyethylene vinyl alcohol solution in substantially the same manner as in Example 1 to coat the overall surface of the hollow fiber with a polyethylene vinyl alcohol. The resultant porous hollow fiber has an average inner diameter of 160 $\mu$m, a membrane thickness of 40 $\mu$m, a porosity of 73%, an average pore diameter of 0.28 $\mu$m, a maximum pore diameter of 0.33 $\mu$m and a water permeability of 5.3 l/hr·m$^2$·mmHg. A bundle of 3000 porous hollow fibers thus obtained is inserted in a cylindrical compact casing having an inside diameter of 18 mm and having, on its side wall, an opening for plasma withdrawal and an opening to be connected to a plasma pressure gauge, and both end portions of the hollow fibers and both end portions of the inner side wall of the compact casing are bonded using a polyurethane resin adhesive in the same manner as in Example 1, so that an average effective length of hollow fibers becomes 73 mm, to thereby obtain a plasma separator. The distance between one end on the blood introduction side of the plasma separator to the other end on the blood withdrawal side of the plasma separator is 125 mm, and the total membrane surface area and the L/D$^2$ value of the hollow fibers of the compact plasma separator are 0.11 m$^2$ and 2900 mm$^{-1}$, respectively. Using the compact plasma separator, an ACD-added fresh bovine blood having a hematocrit (Ht) of 45% and a free Hb concentration of 17 mg/dl is caused to flow through the plasma separator at a blood flow rate (Q$_B$) of 100 ml/min, and the plasma filtration rate (F$_P$) and the plasma collection rate (R$_{PC}$) are measured according to the same method as in Example 1. Further, the blood pressure (A) on the blood introduction side of the plasma separator and the blood pressure (B) on the blood withdrawal side of the plasma separator are measured by means of pressure gauges P$_1$ and P$_2$. From these blood pressures (A) and (B), the pressure loss in the plasma separator is calculated by the formula: $A - B$. Moreover, the hemoglobin (Hb) concentration in the collected plasma is measured in the same manner as in Example 6.

The results are as follows. The plasma filtration rate (F$_P$), the plasma collection rate (R$_{PC}$), the pressure loss in the plasma separator and the hemoglobin (Hb) concentration of the compact plasma separator are 41 ml/min, 75%, 220 mmHg and 17 mg/dl, respectively. As apparent from the results, although the plasma separator prepared above is extremely compact, that is, it has a length of only 125 mm, the plasma collection rate ($R_{PC}$) is as high as 75%. Further, as apparent from the results that there is no difference between the free Hb concentration of the bovine blood and the Hb concentration of the separated plasma, the bovine blood can be stably separated into plasma and blood cellenriched blood without the occurrence of hemolysis.

COMPARATIVE EXAMPLE 7

Using Plasmaflo® AP08H (manufactured and sold by Asahi Medical Co., Ltd., Japan) as a plasma separator, which comprises cellulose diacetate hollow fibers produced by the wet spinning method, the $F_P$ and $R_{PC}$ are determined in the same manner as in Example 11.

The above-mentioned plasma separator AP-08H is large-sized and comprises 4800 hollow fibers having an average inside diameter (D) of 300 μm, an average effective length (L) of 207 mm and a total membrane surface area of 0.8 m². The distance between both ends of the plasma separator is 283 mm and the inside diameter of the casing of the plasma separator is 43.5 mm. The $L/D^2$ value, the $F_P$ and the $R_{PC}$ are 1900 mm$^{-1}$, 32 ml/min and 58%, respectively. Although the total membrane surface area of the plasma separator is extremely large as compared to that of the plasma separator of Example 11, that is, although the membrane surface area of the plasma separator of Comparative Example 7 is as large as 0.8 m², whereas the membrane surface area of the plasma separator of Example 11 is only 0.11 m², the plasma collection rate of the plasma separator of Comparative Example 7 is only 58%, which is significantly lower than that of the compact plasma separator of Example 11, which is 75%.

Example 12

A high-density polyethylene (HI-ZEX 2208J, a product of Mitsui Petrochemical Co., Japan) having a density of 0.968 g/cm³ and a melt index, as measured in accordance with ASTM D1238, of 5.5 is extruded from an annular hollow fiber spinning nozzle having an annular orifice outside diameter of 35 mm and an annular orifice inside diameter of 25 mm (slit width: 5 mm) at an extruding temperature of 150° C. and at a polymer extrusion rate of 15 g/min and a winding rate of 400 m/min. The thus obtained hollow fiber is subjected to annealing at 115° C. for 2 hours. The annealed hollow fiber is then cold-stretched at room temperature at a stretching ratio (the ratio of the length of the stretched hollow fiber to the length of the hollow fiber before stretching, expressed by times) of 1.33 times by passing the annealed hollow fiber through stretching rolls arranged to provide a stretching path of 200 mm. Then, the cold-stretched hollow fiber is hot-stretched successively at 78° C., 92° C. and 95° C. at stretching ratios at 78° C., 92° C. and 95° C. of 3 times, 1.28 times and 1.14 times, respectively. The ratio (%) of the length of the stretched hollow fiber to the original length of the hollow fiber before cold-stretching and hot-stretching is 480%. The thus stretched porous hollow fiber is immersed in a polyethylene vinyl alcohol solution in substantially the same manner as in Example 1 to coat the overall surface of the hollow fiber with a polyethylene vinyl alcohol. The resultant porous hollow fiber has an average inner diameter of 210 μm, a membrane thickness of 50 μm, a porosity of 74%, an average pore diameter of 0.22 μm, a maximum pore diameter of 0.27 μm and a water permeability of 4.7 l/hr·m²·mmHg. A bundle of 2100 porous hollow fibers thus obtained is inserted in a cylindrical compact casing having an inside diameter of 20 mm and having, on its side wall, an opening for plasma withdrawal and an opening to be connected to a plasma pressure gauge, and both end portions of the hollow fibers and both end portions of the inner side wall of the compact casing are bonded using a polyurethane resin adhesive in substantially the same manner as in Example 1 so that the average effective length of hollow fibers becomes 97 mm, to thereby obtain a plasma separator. The distance between one end on the blood introduction side of the plasma separator to the other end on the blood withdrawal side of the plasma separator is 149 mm, and the total membrane surface area of the hollow fibers in the compact plasma separator and the $L/D^2$ value of the hollow fibers are 0.13 m² and 2200 mm$^{-1}$, respectively. Using the compact plasma separator, an ACD-added fresh bovine blood having a hematocrit (Ht) of 40% and a free Hb concentration of 15 mg/dl is caused to flow through the plasma separator at a blood flow rate ($Q_B$) of 100 ml/min. 5 Min, 15 min and 30 min after the initiation of the plasma separation, the plasma filtration rate ($F_P$), the Ht value of the blood cell-enriched cell, the plasma collection rate ($R_{PC}$), the pressure loss in the plasma separator ($\Delta P$) and the hemoglobin (Hb) concentration in the collected plasma are measured according to substantially the same methods as in Example 11. The results are shown in Table 3.

As apparent from the results in Table 3, although the plasma separator prepared above is extremely compact, the plasma collection rate is not decreased with the lapse of time, and 3.5 l of blood can be stably separated into plasma and blood cellenriched blood without the occurrence of hemolysis.

COMPARATIVE EXAMPLE 8

Substantially the same procedure as in Example 12 is repeated except that the hot-stretching temperatures are respectively changed to 96° C., 110° C. and 116° C., to thereby obtain a polyethylene vinyl alcohol-coated hollow fiber. The thus obtained hollow fiber has an average inner diameter of 210 μm, a membrane thickness of 50 μm, porosity of 75%, an average pore diameter of 0.52 μm, a maximum pore diameter of 0.58 μm and a water permeability of 17 l/hr·m²·mmHg.

Using 2000 hollow fibers thus obtained, a compact plasma separator is prepared in substantially the same manner as in Example 12. The membrane surface area of the hollow fibers in the compact plasma separator is 0.13 m², and the $L/D^2$ value of the hollow fiber is 2200 mm$^{-1}$.

Using the compact plasma separator, plasma separation is conducted in substantially the same manner as in Example 12, and the plasma filtration rate ($F_P$), the Ht value of the blood cell-enriched cell, the plasma collection rate ($R_{PC}$), the pressure loss in the plasma separator ($\Delta P$) and the hemoglobin (Hb) concentration in the collected plasma are measured according to substantially the same methods as in Example 11. The results are shown in Table 3.

Since the maximum pore diameter and the average pore diameter are both 0.5 μm or larger, which are extremely large as compared to those of the plasma separator of Example 12, the water permeability of the hollow fiber is high, i.e., 17 l/hr·m²·mmHg, as compared to that of the plasma separator of Example 12 which is 4.7 l/hr·m²·mmHg. As, as apparent from the results in Table 3, however, when the plasma separator of Comparative Example 8 is used, the plasma collection rate is decreased with the lapse of time and hemolysis occurs.

TABLE 3

|  |  | $F_P$ (ml/min) | $Ht^{(1)}$ (%) | $R_{PC}$ (%) | $\Delta P$ (mmHg) | $Hb^{(2)}$ (mg/dl) |
|---|---|---|---|---|---|---|
| Original whole blood | | — | 40 | — | — | 15 |
| Example 12 | | | | | | |
| Blood | 5 | 39 | 67 | 65 | 170 | 16 |
| flowing | 15 | 38 | 64 | 63 | 180 | 16 |
| time (min.) | 30 | 39 | 66 | 65 | 180 | 16 |
| Average | | | 39 | 66 | 65 | 180 | 16 |
| Comparative Example 8 | | | | | | |
| Blood | 5 | 40 | 67 | 67 | 170 | 31 |
| flowing | 15 | 38 | 65 | 63 | 160 | 29 |
| time (min.) | 30 | 26 | 54 | 43 | 120 | 24 |
| Average | | | 37 | 62 | 58 | 150 | 28 |

Note
$^{(1)}$the Ht value of the blood cell-enriched blood.
$^{(2)}$the free hemoglobin concentration of the plasma.

EXAMPLE 14

Using the plasma separator prepared in Example 3, blood is separated into plasma and cell-enriched blood in substantially the same manner as in Example 1 except that the TMP is changed as shown in Table 4, and the plasma filtration rate ($F_P$) is measured. The results are shown in Table 4.

EXAMPLE 15

A hollow fiber is prepared in substantially the same manner as in Example 3 except that the ratio (%) of the length of the stretched hollow fiber to the original length of the hollow fiber before coldstretching and hot-stretching is changed to 400%. The thus prepared hollow fiber has an average inner diameter of 0.24 mm, an average pore diameter of 0.28 μm, a porosity of 66% and a water permeability of 5.8 l/hr·m²·mmHg. From the hollow fiber, a plasma separator is prepared in substantially the same manner as in Example 3. Then, blood is separated into plasma and cell-enriched blood using the plasma separator in substantially the same manner as in Example 14 and the plasma filtration rate ($F_P$) is determined. The results are shown in Table 4.

COMPARATIVE EXAMPLE 9

A hollow fiber is prepared in substantially the same manner as in Example 3, except that the ratio (%) of the length of the stretched hollow fiber to the original length of the hollow fiber before coldstretching and hot-stretching is changed to 250%. The thus prepared hollow fiber has an average inner diameter of 0.24 mm, an average pore diameter of 0.22 μm, a porosity of 60% and a water permeability of 4.4 l/hr·m²·mmHg. From the hollow fiber, a plasma separator is prepared in substantially the same manner as in Example 3. Then, blood is separated into plasma and cell-enriched blood using the plasma separator in substantially the same manner as in Example 14 and the plasma filtration rate ($F_P$) is determined. The results are shown in Table 4.

As apparent from Table 4, when the porosity of the hollow fibers of a plasma separator is 65% or more, the plasma filtration rate ($F_P$) is substantially no longer increased despite the increase in the TMP to more than 50 mmHg. On the other hand, when the porosity is less than 65%, the plasma filtration rate is increased according to the increase of the TMP even when the TMP exceeds 50 mmHg.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

TABLE 4

| | Average inner diameter of hollow fiber (mm) | Porosity of hollow fiber (%) | Average pore diameter of hollow fiber (μm) | Water permeability of hollow fiber (l/m²·hr·mmHg) | $F_P$ (ml/min) | | | | | |
|---|---|---|---|---|---|---|---|---|---|---|
| | | | | | TMP (mmHg) | 0 | 10 | 20 | 40 | 60 | 100 |
| Example 14 | 0.240 | 72 | 0.32 | 6.3 | | 0 | 15 | 17 | 21 | 20 | 20 |
| Example 15 | 0.240 | 66 | 0.28 | 5.8 | | 0 | 11 | 15 | 18 | 19 | 20 |
| Comparative Example 9 | 0.240 | 60 | 0.22 | 4.4 | | 0 | 5 | 8 | 13 | 16 | 18 |

What is claimed is:

1. A compact plasma separator comprising:
   a casing provided with blood introduction means for introducing blood to the casing, blood withdrawal means for withdrawing blood from the casing and at least one opening for plasma withdrawal; and
   a plurality of porous hollow fibers substantially equal in length, said fibers being arranged in a substantially parallel relationship and being bonded together at both end portions thereof to form a bundle, each porous hollow fiber of said bundle having openings at both ends thereof,
   said bundle being disposed in said casing along the length of said casing,
   said both end portions of the hollow fibers of said bundle being fluid-tightly connected to said blood introduction means and said blood withdrawal means, respectively, said blood introduction means and said blood withdrawal means thereby being in communication through said bundle of hollow fibers,
   said porous hollow fibers having an average effective length (L mm) not greater than 200 mm and a membrane surface area (S m²) not greater than 0.3 m²,
   said average effective length (L mm) being defined as an average of the lengths of said porous hollow fibers minus the lengths of said both end portions of said porous hollow fibers at which the fibers are bonded together and fluid-tightly connected to said blood introduction means and said blood withdrawal means, respectively, said membrane surface area (S m$^2$) being defined by the formula:

$$S = n\pi DL \times 10^{-6}$$

wherein n is the number of porous hollow fibers,

L is the average effective length and D is an average inner diameter (mm) of said porous hollow fibers, said average effective length (L mm) and said average inner diameter (D mm) satisfying the following relationship:

$$L/D^2 (mm^{-1}) \geq 2000.$$

2. The plasma separator according to claim 1, wherein each porous hollow fiber comprises a membranous porous resin matrix having pores therewithin and openings on both surfaces thereof, said pores cooperating with said openings to form throughpaths running between both the surfaces of said resin matrix.

3. The plasma separator according to claim 1, wherein said porous hollow fibers have a porosity from 65 to 80%.

4. The plasma separator according to claim 1, wherein said porous hollow fibers have an average pore diameter from 0.1 to 0.5 μm.

5. The plasma separator according to claim 1, wherein said porous hollow fibers have a maximum pore diameter of 0.5 μm or less.

6. The plasma separator according to claim 1, wherein said average inner diameter is in the range from 100 to 316 μm.

7. The plasma separator according to claim 1, wherein said porous hollow fibers are produced by a thermoforming process.

8. The plasma separator according to claim 7, wherein said thermoforming process is a stretching perforation process.

9. A compact plasma separator apparatus comprising:

(a) a compact plasma separator comprising:

a casing provided with blood introduction means for introducing blood to the casing, blood withdrawal means for withdrawing blood from the casing and at least one opening for plasma withdrawal, and a plurality of porous hollow fibers substantially equal in length, said fibers being arranged in a substantially parallel relationship and being bonded together at both end portions thereof to form a bundle, each porous hollow fiber of said bundle having openings at both ends thereof, said bundle being disposed in said casing along the length of said casing, said both end portions of the hollow fibers of said bundle being fluid-tightly connected to said blood introduction means and said blood withdrawal means, respectively, said blood introduction means and said blood withdrawal means thereby being in communication through said bundle of hollow fibers, said porous hollow fibers having an average effective length (L mm) not greater than 200 mm and a membrane surface area (S m$^2$) not greater than 0.3 m$^2$, said average effective length (L mm) being defined as an average of the lengths of said porous hollow fibers minus the lengths of said both end portions of said porous hollow fibers at which the fibers are bonded together and fluid-tightly connected to said blood introduction means and said blood withdrawal means, respectively, said membrane surface area (S m$^2$) being defined by the formula:

$$S = n\pi DL \times 10^{-6}$$

wherein n is the number of porous hollow fibers,

L is the average effective length and D is an average inner diameter (mm) of said porous hollow fibers, said average effective length (L mm) and said average inner diameter (D mm) satisfying the following relationship:

$$L/D^2 (mm^{-1}) \geq 2000;$$

(b) blood introducing passage means for introducing blood to said blood introduction means, said blood introducing passage means comprising a first conduit having one end fluid-tightly connected to said blood introduction means of the plasma separator, a second conduit having a blood inlet at one end thereof, and means for transporting blood, said means for transporting blood being disposed between and fluid-tightly connected to the other ends of said first and second conduits;

(c) blood withdrawing passage means for withdrawing blood from said blood withdrawal means, said blood withdrawing passage means comprising a third conduit having one end fluid-tightly connected to said blood withdrawal means of the plasma separator and having a blood outlet at the other end thereof; and (d) plasma withdrawing passage means for withdrawing plasma from said opening for plasma withdrawal, the plasma withdrawing passage means comprising a fourth conduit having one end fluid-tightly connected to said opening for plasma withdrawal of plasma separator and having a plasma outlet at the other end thereof.

10. The apparatus according to claim 9, wherein each porous hollow fiber comprises a membranous porous resin matrix having pores therein and openings on both surfaces thereof, said pores cooperating with said openings to form throughpaths running between both the surfaces of said resin matrix.

* * * * *